United States Patent [19]

Liu

[11] Patent Number: 5,095,154

[45] Date of Patent: Mar. 10, 1992

[54] TRIVINYL ETHER OF 1,1,1-TRIS(HYDROXYMETHYL) ETHANE

[75] Inventor: Kou-Chang Liu, Wayne, N.J.

[73] Assignee: ISP Investments Inc., Wilmington, Del.

[21] Appl. No.: 632,218

[22] Filed: Dec. 21, 1990

Related U.S. Application Data

[62] Division of Ser. No. 424,419, Oct. 20, 1989, abandoned.

[51] Int. Cl.$^5$ .............................................. C07C 41/08
[52] U.S. Cl. .................................................. 568/673
[58] Field of Search ......................................... 568/673

[56] References Cited

U.S. PATENT DOCUMENTS 3,657,360  4/1972  Carluccio et al. ................... 568/673
4,751,273  6/1988  Lapin et al. ...................... 568/673 X

*Primary Examiner*—Howard T. Mars
*Attorney, Agent, or Firm*—Walter Katz; Marilyn J. Maue; Joshua J. Ward

[57] ABSTRACT

What is provided herein is a multifunctional vinyl ether monomer having the formula:

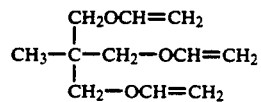

which is the trivinyl ether of 1,1,1-tris(hydroxymethyl) ethane.

1 Claim, No Drawings

TRIVINYL ETHER OF 1,1,1-TRIS(HYDROXYMETHYL) ETHANE

This is a division of application Ser. No. 424,419, filed Oct. 20, 1989 abandoned.

BACKGROUND OF THE INVENTION

1. Field of the Invention

This invention relates to multifunctional vinyl ethers, and more particularly, to trivinyl ether monomers and resin formulations thereof useful in applications which require high speed cationic initiated radiation curing.

2. Description of the Prior Art

Vinyl ether compounds, and methods for effectively cationically polymerizing such compounds, have been described in the literature. See, for example, U.S. Pat. Nos. 4,161,405; 4,518,788; 4,751,273; 4,775,732; and 4,749,807. However, the art is limited with respect to multifunctional vinyl ether monomers and to methods for their preparation.

Accordingly, it is an object of this invention to provide a new and useful multifunctional vinyl ether monomer which is advantageous for use in various commercial applications.

DESCRIPTION OF THE INVENTION

What is provided herein is a multifunctional vinyl ether monomer having the formula:

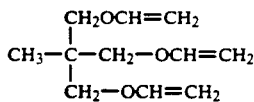

which is the trivinyl ether of 1,1,1-tris(hydroxymethyl) ethane.

The monomer may be prepared by direct vinylation of 1,1,1-tris(hydroxymethyl) ethane with acetylene. In the batch form of the reaction, the mole ratio of polyol to acetylene can vary between about 1:3 and about 1:4.5. In the batch or continuous form of the process, the acetylene gas is bubbled through the polyol liquid itself, or a solution of the polyol in a suitable solvent, such as the dimethyl ether of tetraethylene glycol. Other methods of preparation also may be used for synthesis of the compound of the invention, such as catalytic transetherification of the polyol with a suitable vinyl ether having a boiling point higher than the monomer product.

The acetylene can be introduced into the reaction zone without dilution if present at low pressures; however, at elevated pressures, it is recommended that an inert non-oxygen containing gaseous diluent, such as nitrogen, a $C_1$–$C_3$ alkane or helium be used to dilute the acetylene reactant. When a diluent is employed, an acetylene concentration as low as 10% can be used, although between about 40 and about 60 wt. % acetylene in a diluent is most preferred.

The reaction is carried out in an oxygen free atmosphere which is generally achieved by purging with nitrogen and in the presence of a basic catalyst, such as an alkali metal hydroxide, e.g. potassium hydroxide, sodium hydroxide, and sodium, potassium or lithium metal, or hydride thereof. The concentration of catalyst employed can range from about 0.01% to about 5% by weight.

The process is effected at a temperature of between about 120° and about 180° C., under from about 10 to about 200 psig. total pressure, in a period of from about 2 to about 100 hours reaction time. Preferred conditions include a temperature of between about 140° to about 170° C., under between about 50 and about 100 psig. acetylene pressure and a reaction period of from about 4 to 70 hours.

EXAMPLE

Tris(hydroxymethyl) ethane (1201.5 g), tetraethylene glycol dimethyl ether (1000 g) and potassium hydroxide, 85% pellets (30 g) were charged into a one-gallon autoclave. The autoclave was purged three times with nitrogen, heated to 110° C. and held under vacuum at 20 mm Hg for 10 minuts. Propane (100 psig.) was then added and the temperature was raised to 140° C. The propane pressure was readjusted to 100 psig. and acetylene (100 psig.) was introduced to start the vinylation. The reaction was complete in 62 hours. The autoclave was then cooled to room temperature, purged two times with nitrogen and discharged. 2797 g of crude product was obtained which contained 86.4% of the trivinyl ether of tris(hydroxymethyl) ethane, as determined by glc analysis.

The crude product (2788 g) was distilled with a 30 plates Oldershaw column at a reduced pressure of 7 mm Hg. A total of 646.9 g of the trivinyl ether of tris(hydroxymethyl) ethane with 99% purity was collected between 69° and 71° C. The structure of the trivinyl ether was identified by nmr analysis.

FIELDS OF USE

The compound of the invention exhibits a high speed cationic initiated radiation curing property, which enables its use in applications which require high speed curing, such as radiation curable coatings, photoresists in the electronic industry, and printing inks, which applications require ultraviolet or electronic beam activation.

It is to be understood that the above examples are provided to illustrate specific and preferred embodiments of the invention and that many modifications and alterations can be made in these examples without departing from the scope of the invention.

What is claimed is:

1. A process for making the trivinyl ether of 1,1,1-tris(hydroxymethyl)ethane in a yield of 86% which is characterized by direct vinylation of tris(hydroxymethyl)ethane at 140° C., in the presence of 2% by weight of KOH based upon said tris(hydroxymethyl)ethane as a catalyst, at 100 psi. acetylene pressure, in an inert gas at the same pressure as the acetylene, at a mole ratio o said tris(hydroxymethyl)ethane to said acetylene of 1:3 and isolation of the product in a purity of 99% of 69°–71° C. by distillation under a reduced pressure of 7 mm.